(12) United States Patent
Terrell

(10) Patent No.: US 11,039,946 B2
(45) Date of Patent: Jun. 22, 2021

(54) NON-SURGICAL METHOD AND APPARATUS FOR TREATING CARPAL TUNNEL SYNDROME

(71) Applicant: Thomas Terrell, Brookhaven, MS (US)

(72) Inventor: Thomas Terrell, Brookhaven, MS (US)

(*) Notice: Subject to any disclaimer, the term of this patent is extended or adjusted under 35 U.S.C. 154(b) by 401 days.

(21) Appl. No.: 15/918,631

(22) Filed: Mar. 12, 2018

(65) Prior Publication Data
US 2019/0274857 A1 Sep. 12, 2019

(51) Int. Cl.
| | | |
|---|---|---|
| *A61F 5/04* | (2006.01) | |
| *A61F 5/01* | (2006.01) | |
| *A41D 19/00* | (2006.01) | |
| *A61F 5/30* | (2006.01) | |
| *G01L 5/00* | (2006.01) | |
| *G01L 5/04* | (2006.01) | |
| *A61F 5/37* | (2006.01) | |

(52) U.S. Cl.
CPC ........ *A61F 5/0118* (2013.01); *A41D 19/0037* (2013.01); *A61F 5/30* (2013.01); *A61F 5/3723* (2013.01); *G01L 5/0038* (2013.01); *G01L 5/045* (2013.01); *A41D 2400/32* (2013.01)

(58) Field of Classification Search
CPC .. A61F 5/118; A61F 5/012; A61F 2005/0167; A61F 5/34; A61F 5/05866; A61F 5/05841; A61F 5/30; A41D 19/0037; A41D 2400/32; G01L 5/0038; G01L 5/045; A63B 21/00058; A63B 21/00178; A63B 21/002; A63B 21/0023; A63B 21/4017; A63B 21/4019; A63B 21/4021; A63B 21/4023; A63B 21/4025; A63B 21/4011; A63B 21/4013; A63B 21/4015; A63B 21/4027; A63B 21/4043; A63B 21/4045; A63B 21/00069; A63B 21/00076; A63B 21/00181; A63B 21/005; A63B 21/0552; A63B 21/0555; A63B 21/0557

See application file for complete search history.

(56) References Cited

U.S. PATENT DOCUMENTS

| | | | | |
|---|---|---|---|---|
| 3,510,132 A | * | 5/1970 | Holkesvick | ...... A63B 21/00069 482/120 |
| 5,306,222 A | * | 4/1994 | Wilkinson | ....... A63B 21/00069 482/124 |
| 6,203,473 B1 | * | 3/2001 | Atwood | ........... A63B 21/00047 482/142 |

(Continued)

*Primary Examiner* — Ophelia A Hawthorne
*Assistant Examiner* — Camtu T Nguyen
(74) *Attorney, Agent, or Firm* — Lamon Patent Services; Cynthia S. Lamon

(57) ABSTRACT

A method includes providing a strap having a length enabled to encircle one side of a user's hand and tricep area when the user's elbow is bent at 90°, and creating a loop with the strap. The loop closing with a buckle, and positioning the inside of one end of the loop around a ventral or dorsal portion of a user's hand or fingers. A step is provided for positioning the inside flat surface of a second end of the loop around at an area at a back side of the user's upper arm, above the elbow, with the elbow bent at approximately 90 degrees. The strap is then tightened to achieve an effective stretch as determined by the user and the stretch may be held for a determined amount of time thereby increasing strength and flexibility and lessen pain in the user's hand, wrist and forearm.

9 Claims, 12 Drawing Sheets

(56) References Cited

U.S. PATENT DOCUMENTS

| | | | | |
|---|---|---|---|---|
| 2006/0282033 | A1* | 12/2006 | Zeide | A61F 5/373 602/20 |
| 2009/0272007 | A1* | 11/2009 | Beers | A43C 11/14 36/50.1 |
| 2017/0274236 | A1* | 9/2017 | Farias | A63B 21/0023 |

* cited by examiner

NON-SURGICAL METHOD AND APPARATUS FOR TREATING CARPAL TUNNEL SYNDROME

BACKGROUND OF THE INVENTION

1. Field of the Invention

This invention relates to a device and method for the treatment of pain, stiffness and flexibility in the hands and wrist, primarily carpal tunnel syndrome and treatment of symptoms associated with carpal tunnel syndrome and other similar conditions. Additionally, this invention maintains healthy status of hands, wrist and forearms of individuals involved in high stakes and necessary repetitive use of said limbs.

2. Discussion of the State of the Art

Carpal tunnel syndrome, as well as other painful conditions involving hands, wrists and arms, commonly afflict persons involved with repetitive movement from sports, employment and other types of repetitive movement involving the hand, wrist and arm. For example, carpal tunnel syndrome is predominant in work environments involving handling objects on conveyer belts, using screw drivers, punching a ratchet, hand weeding, line cooks and even typists. Sports that involve repetitive pressure or strain on the wrists, for example basketball, may also cause the condition, and some wrist injuries may also cause the condition. Some other conditions that may cause carpal tunnel syndrome include inflammation caused by pregnancy, edema or obesity. Anomalous muscle development in hands, wrist and upper arm muscles may also cause or exaggerate the syndrome.

Extreme pain, tingling and numbness are common symptoms of carpal tunnel syndrome in the fingers or hand, especially the thumb and index, middle or ring fingers. Weakness is also a common symptom causing carpal tunnel syndrome sufferers to drop objects, or perhaps not be able to handle a steering wheel or other dangerous equipment properly.

Current methods of treatment for carpal tunnel syndrome, as known in the art, include surgery, pain medications including opiates and steroids. The inventor of the present invention understands that with regular treatment involving the surrounding tendons, muscles and bones of the Carpal tunnel, inflammation can be reduced relaxing the tunnel while taking pressure off of the Median nerve in the process. With the method of treatment proposed in the present invention, carpal tunnel syndrome can be prevented and significantly reduced without costly surgery, drugs and steroids.

De Quervain's condition is a condition very similar to carpal tunnel syndrome. De Quervain's happens as a result of repetitive use of excessive gripping in a sideways motion, or in pinching forces of the thumb and wrist. This condition is usually found in computer operators, musicians and people involved with racket sports. Many repetitive activities in the office setting can also contribute to de Quervain's. While typing, moving the wrist continually toward the small finger or always contracting the thumb muscles over the keyboard space bar are two examples. Forceful motions while filing and continuous tight holding of a writing instrument are types of pinching forces that may contribute to de Quervain's.

BRIEF SUMMARY OF THE INVENTION

The present invention provides a method in one embodiment enabling relief of at least carpal tunnel syndrome, arthritis and other ailments of a user's hands, wrist and forearm. The steps for performing the invention begin with providing a strap having a length enabled to encircle one side of a user's hand and tricep area of the user's arm when the user's elbow is bent at approximately 90°. In this embodiment a loop is created with the strap, the loop having an inside flat surface and an outside flat surface. The loop is then closed with a buckle, weaving one end of the strap through the buckle and securing a second end of the strap at the buckle.

The strap is then positioned at an inside surface of one end of the loop around a ventral portion of a user's hand at an area crossing the user's proximal interphalangeal joint and distal interphalangeal joint on index, middle, ring and pinky fingers, as the fingers are pointing away from the user and positioning the inside flat surface of a second end of the loop around at an area at a back side of the user's upper arm, above the elbow, with the elbow maintaining the bent position at approximately 90 degrees.

The strap is tightened in order to achieve an effective stretch as determined by the user and the stretch is held for a predetermined or desired amount of time and repeating previous steps, as required, to increase strength and flexibility and lessen pain in the user's hand, wrist and forearm.

In one embodiment the fingers are pointed towards the user. In another embodiment, the loop is placed around a dorsal side of a user's hand across an area including the user's metacarpophalangeal joints of index, middle, ring and pinky fingers with fingers pointed towards user, prior to tightening. The fingers may also be pointed away from the user in this embodiment.

An additional embodiment provides that the strap is connected at one end to a ratchet, and a second end is weaved through the ratchet enabling a handle of the ratchet to manipulate movement of the second end causing the strap to tighten, holding the second end of the strap in place, thereby decreasing a circumference of the loop. A torque or force meter may be attached on the strap enabling force in pounds to be determined as a result of tightening. Optionally, a timer is implemented in the method in order to record a time frame while the user holds the stretch.

One embodiment provides a pad implemented between the inside flat surface of the strap and the area at a back side of the user's upper arm, above the elbow. A glove may also be added in another embodiment, prior to positioning the loop prior to tightening. The glove may be made from material that adheres to the user's skin, such as silicon or rubber, and includes may include a VELCRO™ strip between the strap and the area on the ventral and dorsal sides of the user's hand.

DETAILED DESCRIPTION OF THE INVENTION

Figure 1:
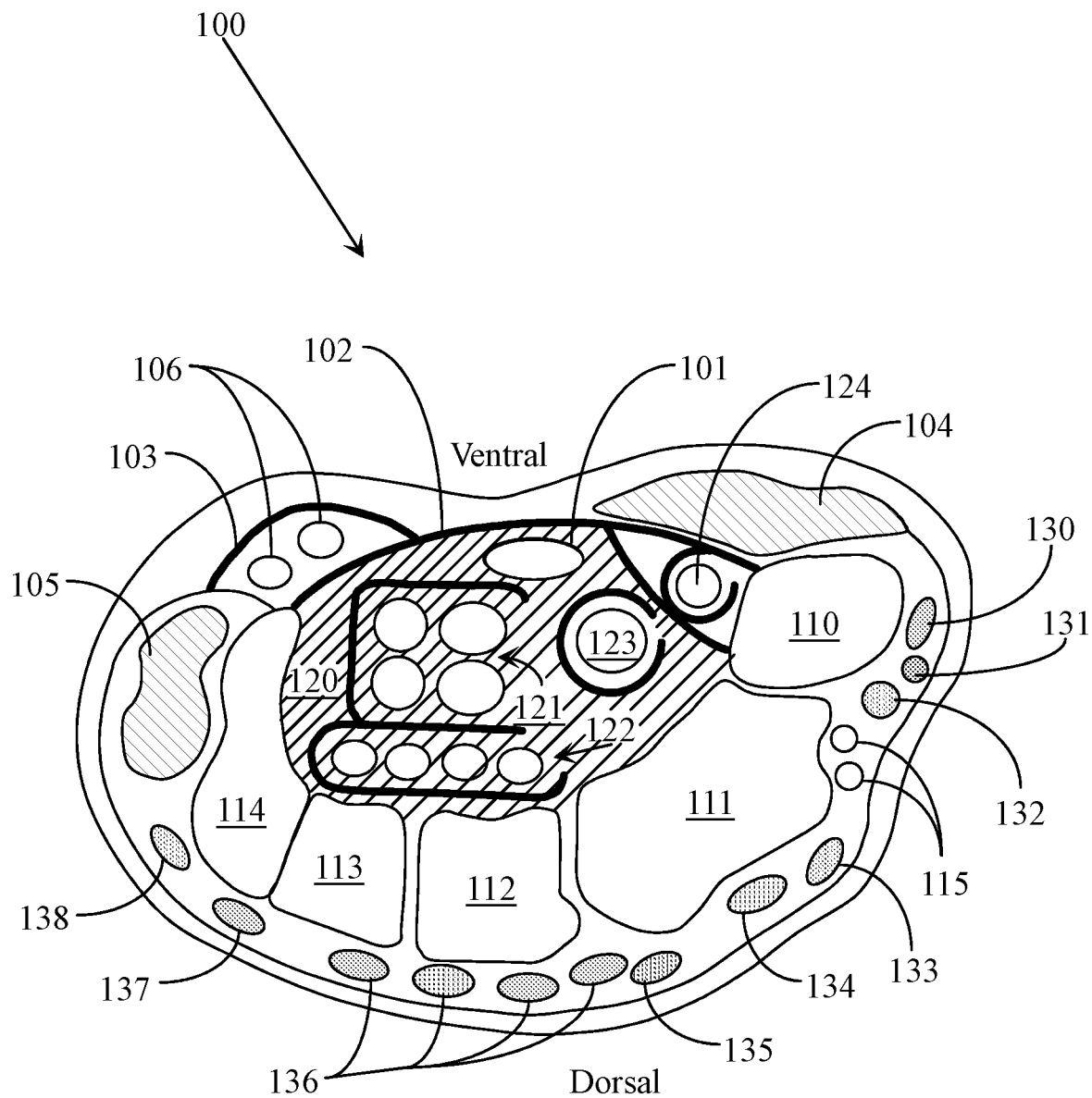
FIG. 1 is an interior cross-section view of the carpal tunnel of a human wrist.

FIG. 1 depicts an interior cross section of elements of a human wrist 100 having a ventral side and dorsal side. As a guide in presenting elements of the wrist and their functions in their effect on the carpal tunnel, general categories of elements will first be introduced. Flexor muscles are skeletal muscles that contract to bend a joint decreasing an angle between components of a limb, for example straightening a wrist where the hand is bent upwards in relation to the wrist. This action is known as flexion. Extensor muscles work in an opposite fashion to increase an angle between components of a limb, for example when the wrist is turned under the forearm. These actions are called extensions.

Working together these muscles flex the hand at the wrist. FIG. 1 includes a thenar eminence 104 which refers to the group of muscles on the ventral side of the human hand at the base of the thumb. Nine flexor tendons 121-123 pass through the carpal tunnel 120 positioned below 104. The flexor carpi radialis tendon 124 is associated with the muscle of the same name which abducts the hand toward the thumb. The other three flexor muscles are associated with the their respective tendons passing through the carpal tunnel, being the flexor digitorum superficialis 121, flexor digitorum profundus 122 and flexor pollicis longus 123. These muscles extend from the bones of the arm and forearm and insert into the phalanges of the hand to flex the fingers and thumb, respectively. The tendons of the flexor muscles and the median nerve 101 also pass through the carpal tunnel.

A plurality of long thin extensor muscles are found in the posterior side of the forearm extend the hand and fingers. The extensor carpi radialis longus 133 originates at the elbow at the lateral epicondyle of humerus and inserts at the third metacarpal (middle finger). The extensor carpi radialis brevis 134 is closely connected with that of the extensor carpi radialis longus, and accompanies it to the wrist, it passes beneath the abductor pollicis longus 130 and extensor pollicis brevis 131, beneath the extensor retinaculum 102, and inserts into the lateral dorsal surface of the base of the third metacarpal bone (middle finger). The extensor carpi ulnaris 138 originates from the lateral epicondyle of the humerus and the posterior border of the ulna, and crosses the forearm to the ulnar (medial) side to insert at the base of the 5th metacarpal (pinky finger). It is important to keep in mind that the radialis muscles abduct the hand and the ulnaris adducting it and are largely responsible for movement of the wrist.

Several muscles in the forearm (not shown) control the pivoting of the radius around the ulna that rotates the wrist and hand. The supinator muscle inserts on the radius and supinates the hand by turning the palm upwards or toward the front of the body. Working as antagonists to the supinator, the pronator teres and pronator quadratus muscles pronate the hand by turning it posteriorly or palm side down. The pronator muscles both insert on the opposite side of the radius from the supinator so that each set of muscles can rotate the radius in opposite directions.

The carpal tunnel 120 is defined on the ventral side of the wrist by the Flexor retinaculum 102, a transverse carpal ligament, splitting off to compartmentalize the Flexor carpi radialis 124. and on the dorsal side by five wrist bones, the Trapezium 110, Trapezoid 111, Capitate 112, Hamate 113 and Triquetrum 114 with the extensors overlaying the wrist bones.

Carpal tunnel syndrome is commonly known to result from pressure on a Median nerve 101 that passes through the Carpal tunnel 120. The median nerve 101 originates from the lateral and medial cords of the brachial plexus (shoulder area) through the carpal tunnel to the middle, index, ring and thumb. Other structures within the Carpal tunnel include Flexor digitorum superficialis tendons 121, attached to a forearm muscle with the same name, which pass through the tunnel and attach at the middle phalanx at the index, middle and ring fingers. Flexor digitorum profundus 122 tendons that are part of a forearm muscle running underneath the Flexor digitorum superficialis, also run through the Carpal tunnel. A flexor pollicis longus 123 is a muscle in the forearm and hand, flexing the thumb and having tendons that pass through the Carpal tunnel as well as the Flexor carpi radialis 124, which is another forearm muscle that acts to flex and (radial) and abduct the hand.

The flexor retinaculum 102 is particularly important because of its close proximity to the carpal tunnel 120, especially the median nerve 101. 102 is a strong, fibrous band that covers the carpal bones on the palmar side of the hand near the wrist attaching at least to the medial part of the palmar surface and the ridge of the trapezium 110.

The flexor retinaculum 102 is continuous with the palmar carpal ligament 103, and the ulnar artery and ulnar nerve, and the cutaneous branches of the median and ulnar nerves, pass on top of the flexor retinaculum. On the radial side of the retinaculum is the tendon of the flexor carpi radialis, which lies in the groove on the greater multangular between the attachments of the ligament to the bone.

The tendons of the palmaris longus and flexor carpi ulnaris are partly attached to the surface of the retinaculum; below, the short muscles of the thumb and little finger originate from the flexor retinaculum.

In carpal tunnel syndrome (CTS), one of the tendons or tissues in the carpal tunnel is inflamed, swollen, or fibrotic and puts pressure on the other structures in the tunnel, including the median nerve. Repetitive motion of the flexor tendons can cause them to become inflamed and impinge the median nerve 101, leading to pain, numbness and tingling leading to carpal tunnel syndrome.

Carpal tunnel syndrome may be treated surgically; although this is usually done after all non-surgical methods of treatment have been exhausted. Non-surgical treatment methods include aspirin and other anti-inflammatory drugs. Additionally, the wrist may also be immobilized in order to prevent further use and inflammation. When surgery is needed, the flexor retinaculum 102 is either completely severed or lengthened.

An object of the present invention is to provide an apparatus and method of stretching and strengthening all of the muscles, tendons and ligaments listed above in the forearm wrist and hand in multiple directions (flexion and extensions) keeping the components 101-138, especially flexor reticulum 102 flexible and loose thereby preventing or lessening inflammation and tightening of the carpal tunnel 120. Additionally, stretching and strengthening components 106 within the palmar carpal ligament 103 and areas around 130-132, 115, 133-138 next to wrist bones 110-114 helps to keep the carpal tunnel open and lends to overall health of the wrist in general, thereby preventing CTS from occurring. Additionally, the apparatus and method may also treat and prevent arthritis pain and pain from normal wear and tear, or over use of the hands and wrist.

Figure 2A:
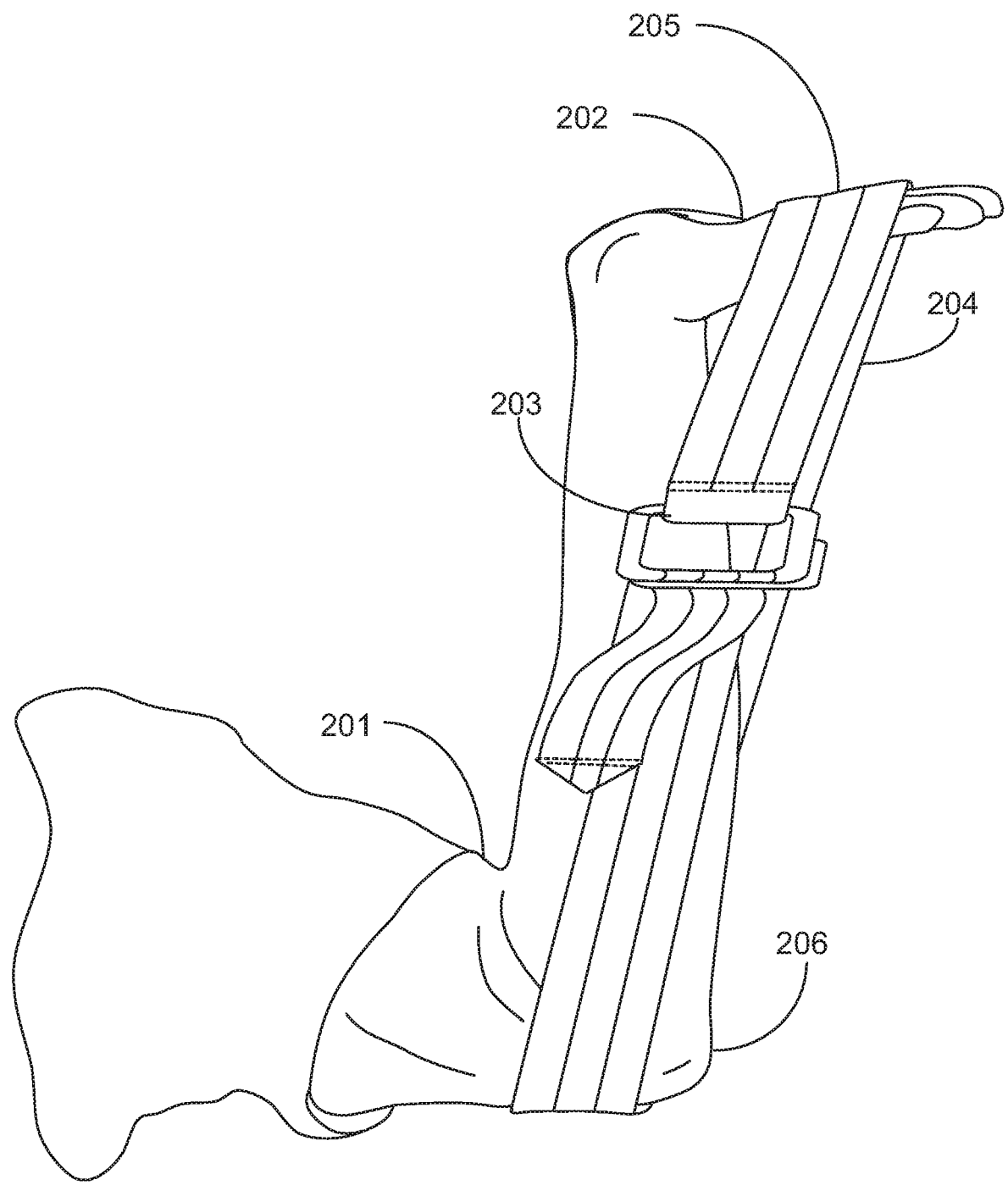
FIG. 2A is a perspective view of an apparatus implemented in an aspect of a treatment method for at least carpal tunnel syndrome.

FIG. 2A shows an example of an apparatus and method for preventing or alleviating symptoms associated with carpal tunnel syndrome as well as other medical conditions of the wrist causing pain, such as De Quervain's condition or any other hand, wrist condition. In this embodiment, circular enclosed strap or belt 204 is shown laying flat against an area finger position 205 above palm 202 extending down to encompass a position just inside a person's elbow 206. Belt 204 may be manufactured from synthetic or natural elastic or non-elastic material including cotton, nylon, polyester, hemp, bamboo, etc. a width of the belt may range from 2.5 cm to 10.5 cm and the length would be approximately between 63.5 cm and 114.5 cm as required to encompass a child or adult person's arm between fingers and elbow. Tension of the belt may be adjusted by buckle 203 which serves to keep the belt closed in a loop without allowing belt material to slide through it. Buckle 203 may be made from metal, plastic or any other rigid material capable of maintaining closure of belt 204, under tension. The buckle 203 is positioned on the strap to be accessible and operated by one hand of the user, the hand that does not engage the strap during use. The buckle 203 may be a slide buckle, but may be any one of a side release, clamp, cam lock ratchet or jam lever buckle.

A person's arm is bent at joint 201 in this embodiment depicting the belt stretching the finger position down towards the elbow and away from the person. This position stretches the components of FIG. 1 on the ventral side of the wrist including 104, 105, 103, 106, 102, 101, 124, 123, 121 and 122. The stretch is especially effective as it originates at the finger position instead of the palm, thereby incorporating more components into the stretch. This stretch is held for a period of time and may be repeated. When a loose end of the strap or belt is pulled the loop tightens thereby decreasing a circumference of the loop.

Figure 2B:
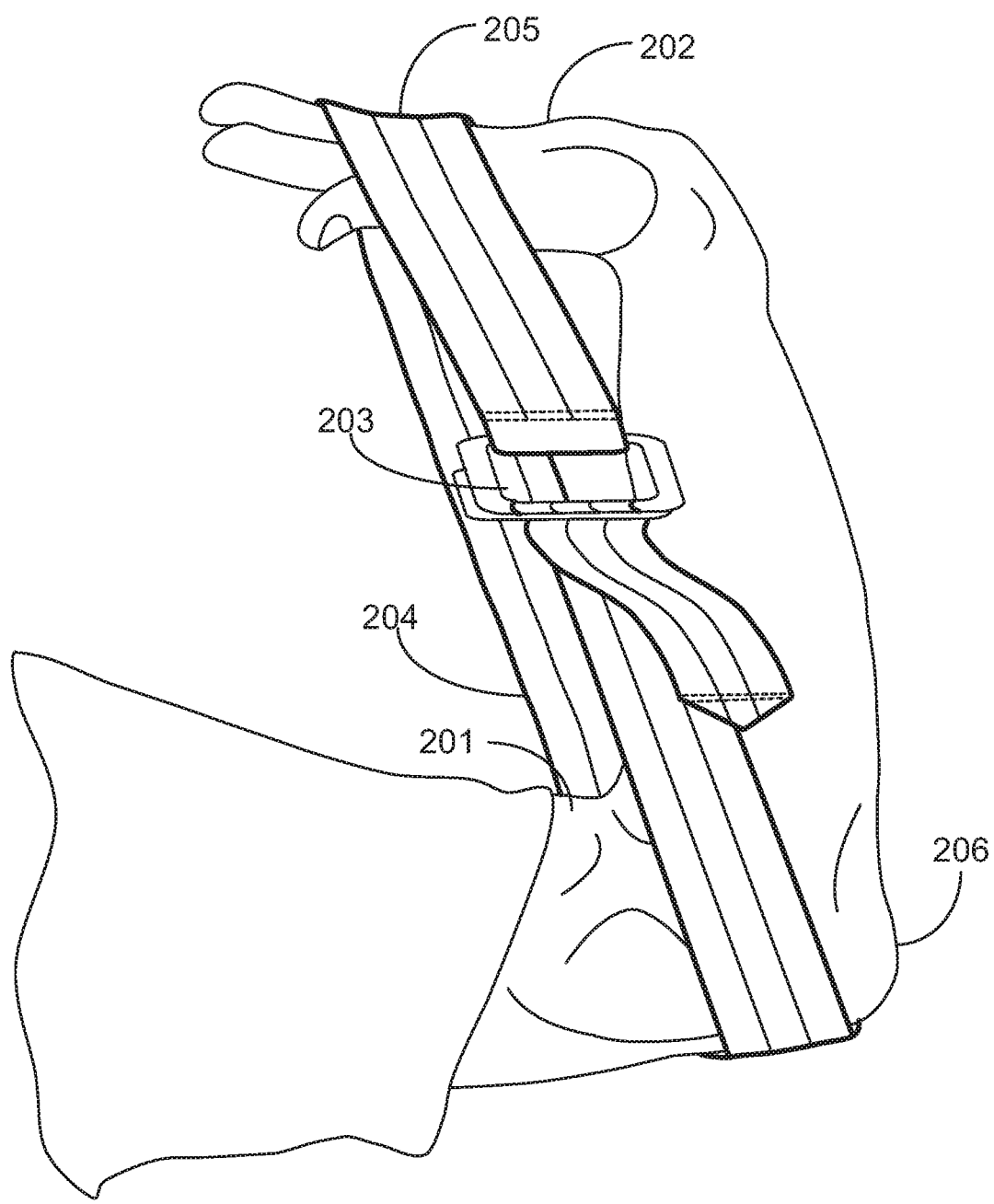
FIG. 2B is another aspect of the treatment method.

FIG. 2B shows another embodiment wherein belt 203 is positioned as in FIG. 2A only the fingers are pointed towards the person which may incorporate different components 104, 105, 103, 106, 102, 101, 124, 123, 121 and 122 and/or stretch the components in an alternate direction than that of FIG. 2A, thereby increasing strength and flexibility. Additionally the stretches embodied in FIGS. 2A and 2B include stretching forearm muscles (not shown) having origination or attachment points at or near the components thereby affecting the stretch, flexibility and strength of those components contributing to the overall health of the wrist and fingers.

Figure 3:
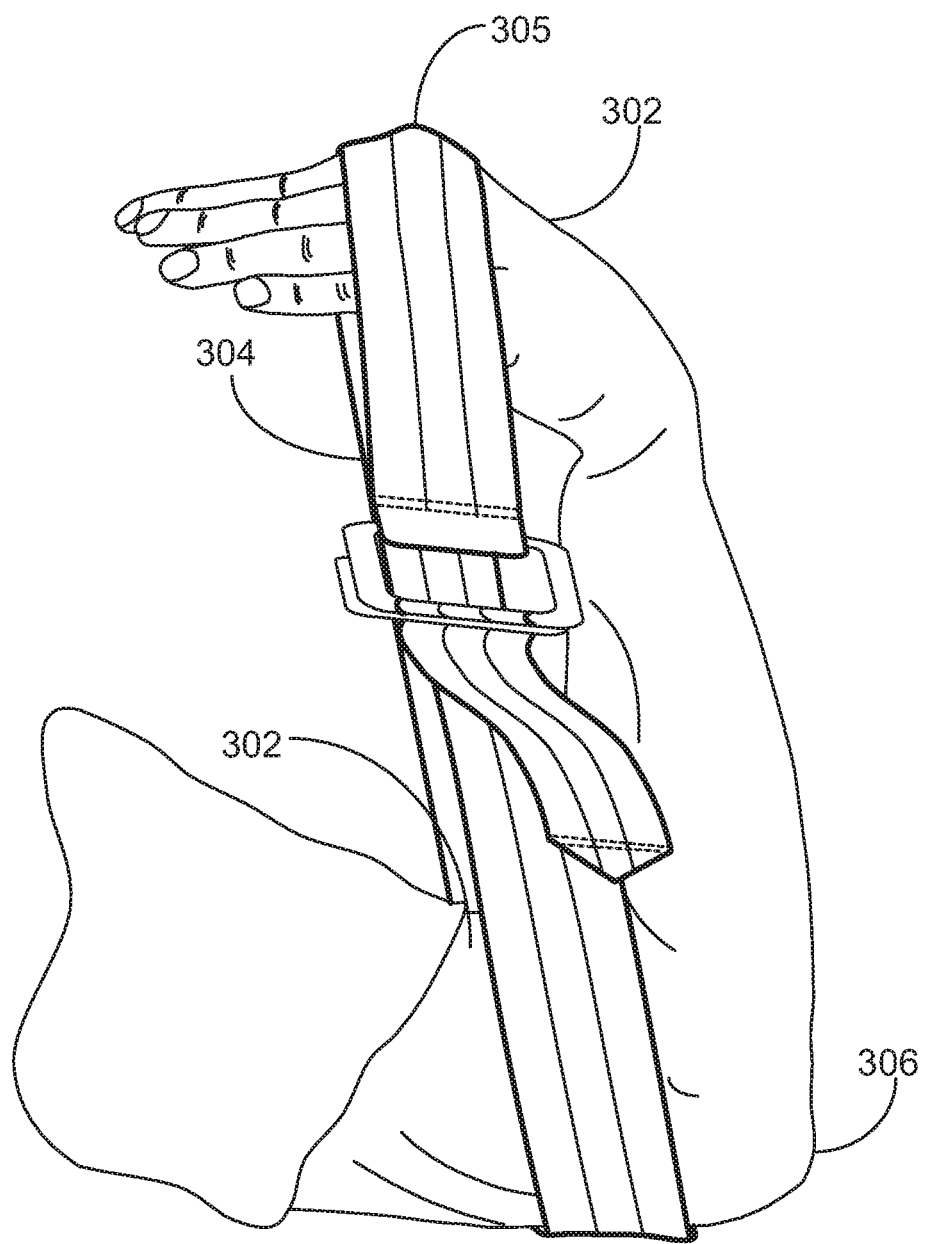
FIG. 3 is an alternate perspective of an apparatus implemented in the treatment method.
Figure 4:
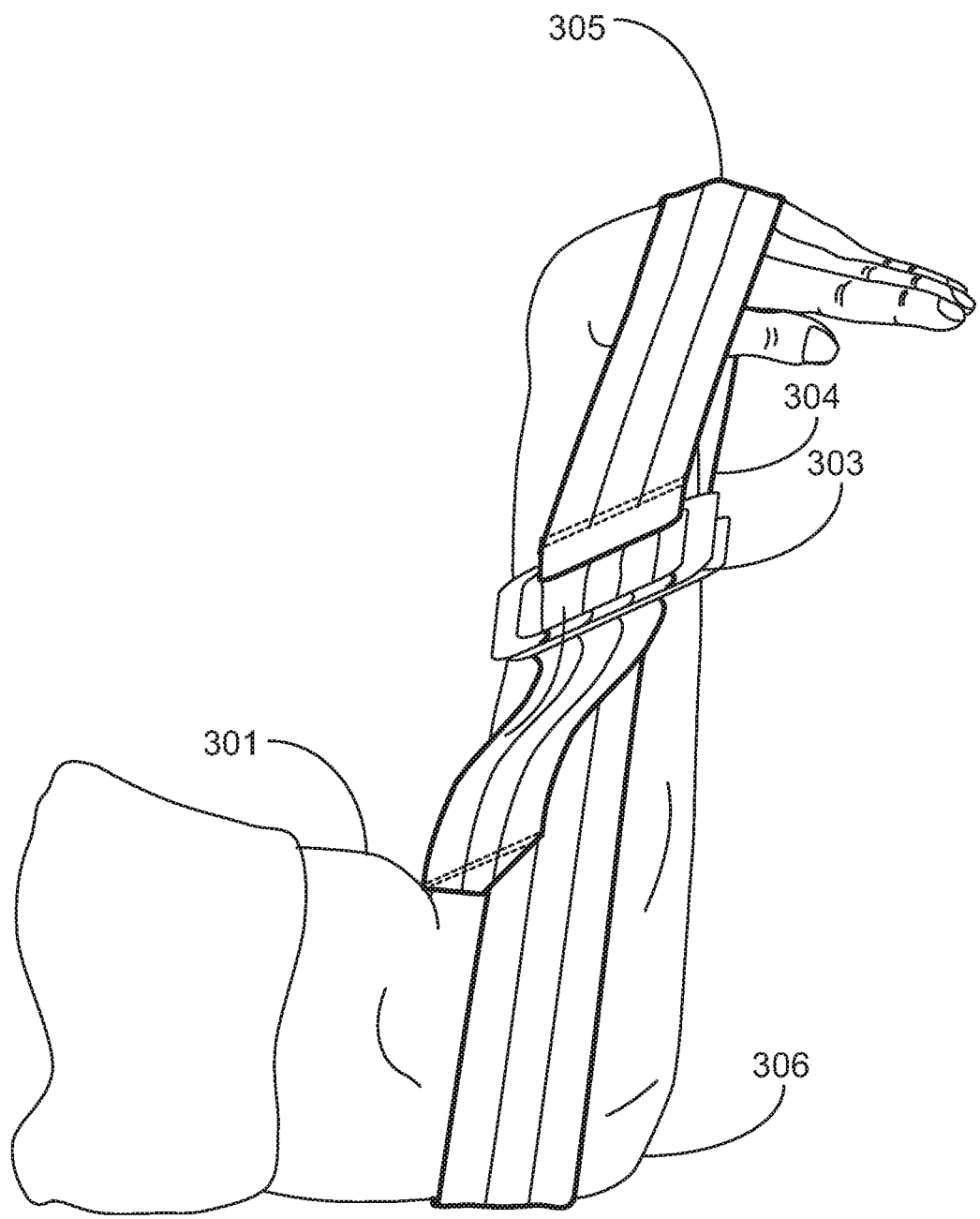
FIG. 4 is another alternate view of the apparatus implemented in the treatment method.

FIG. 3 shows use of the apparatus and method wherein the belt 304 is looped and positioned on a dorsal side 302 of the hand across the major knuckles or metacarpophalangeal at position 305. The elbow 306 is bent toward bicep 302 and fingers of hand 302 are pointed towards the person. FIG. 4 shows the same configuration of FIG. 3 only fingers of the hand are pointed away from the user, thereby benefitting from bi-directional stretching of forearm muscles directly or indirectly attached to wrist components, as discussed above.

Figure 5A:
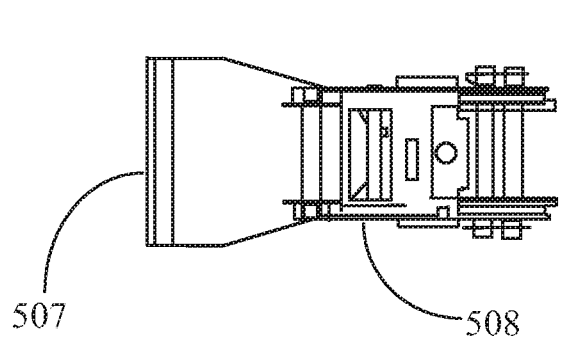
FIG. 5A-5B are perspective views of the apparatus including a ratchet clamp implemented in the method of treatment.
Figure 5B:
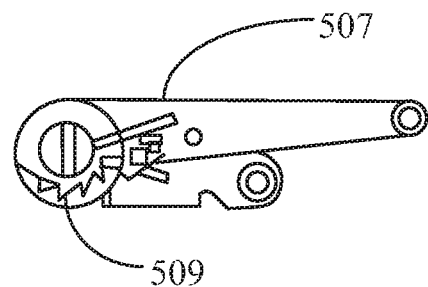

FIG. 5A shows a ratchet 507 enabling precise integral tightening of belt 503 (FIG. 5C) by operation of ratchet handle 508. During operation, viewing FIG. 5B, teeth 509 of the ratchet clamp down on the belt in order to move belt material incrementally while operating handle 507. The belt is held in position by ratchet 508 after belt tension is reached by handle 507. Ratchet 507 may enable precise tightening of the belt that is not possible by hand tightening of the belt via buckle 303.

Figure 5C:
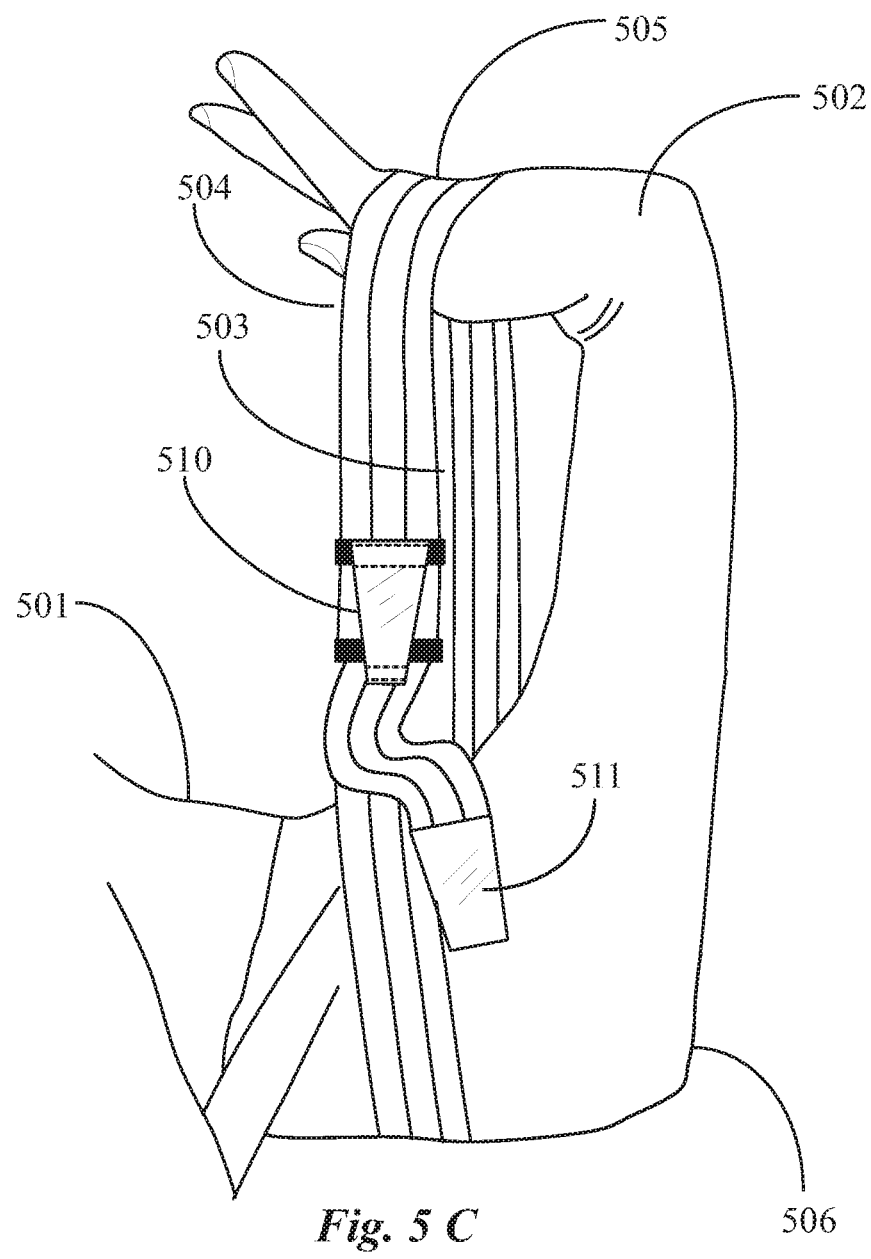
FIG. 5C is a perspective view of the ratchet clamp in place on the apparatus during use.

FIG. 5C shows use of the apparatus and method 500 implementing ratchet 508. In use, a belt end 511 is weaved through ratchet 508 enabling handle 507 and teeth 509 to position the belt at the optimum tension required for treatment involving stretching. In this example the person's arm is bent at elbow 506, an inside surface 504 of the belt engages with a portion of the user's arm at an opposite side of the bicep 501 and the belt loops around a person's hand at position 505. The belt end 511 feeds through ratchet 510 and teeth 509 of FIG. 5B clamp onto an outside surface 503 of the belt. Position of the belt and proper therapeutic tension is reached by operation of handle 507 of the ratchet which tightens the belt thereby decreasing a circumference of a loop formed around the users hand and area near and above the elbow. This position may be held for an amount of time deemed effective for a stretch.

Figure 6A:
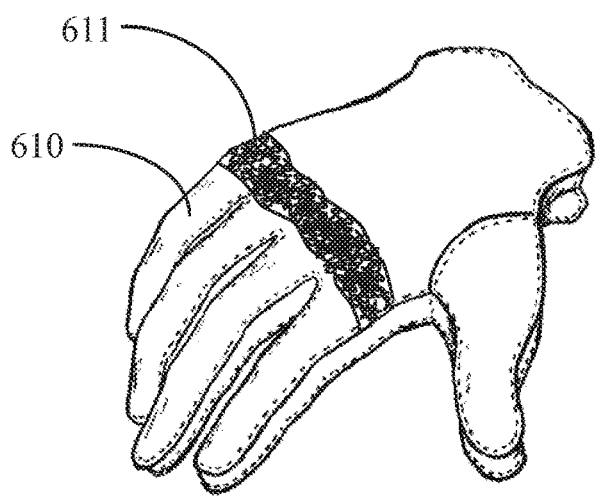
FIG. 6A is a dorsal perspective view of an attachment glove to be used with the apparatus
Figure 6B:
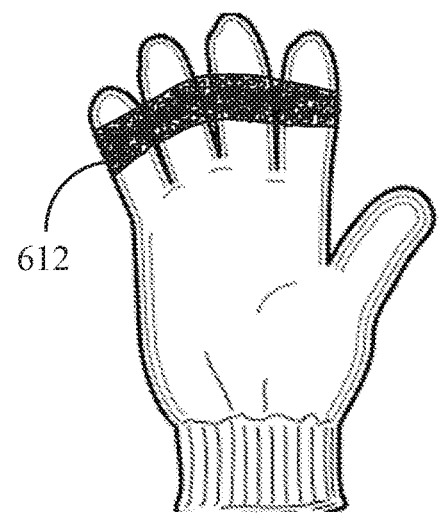
FIG. 6B is a ventral perspective view of an attachment glove to be used with the apparatus.
Figure 6C:
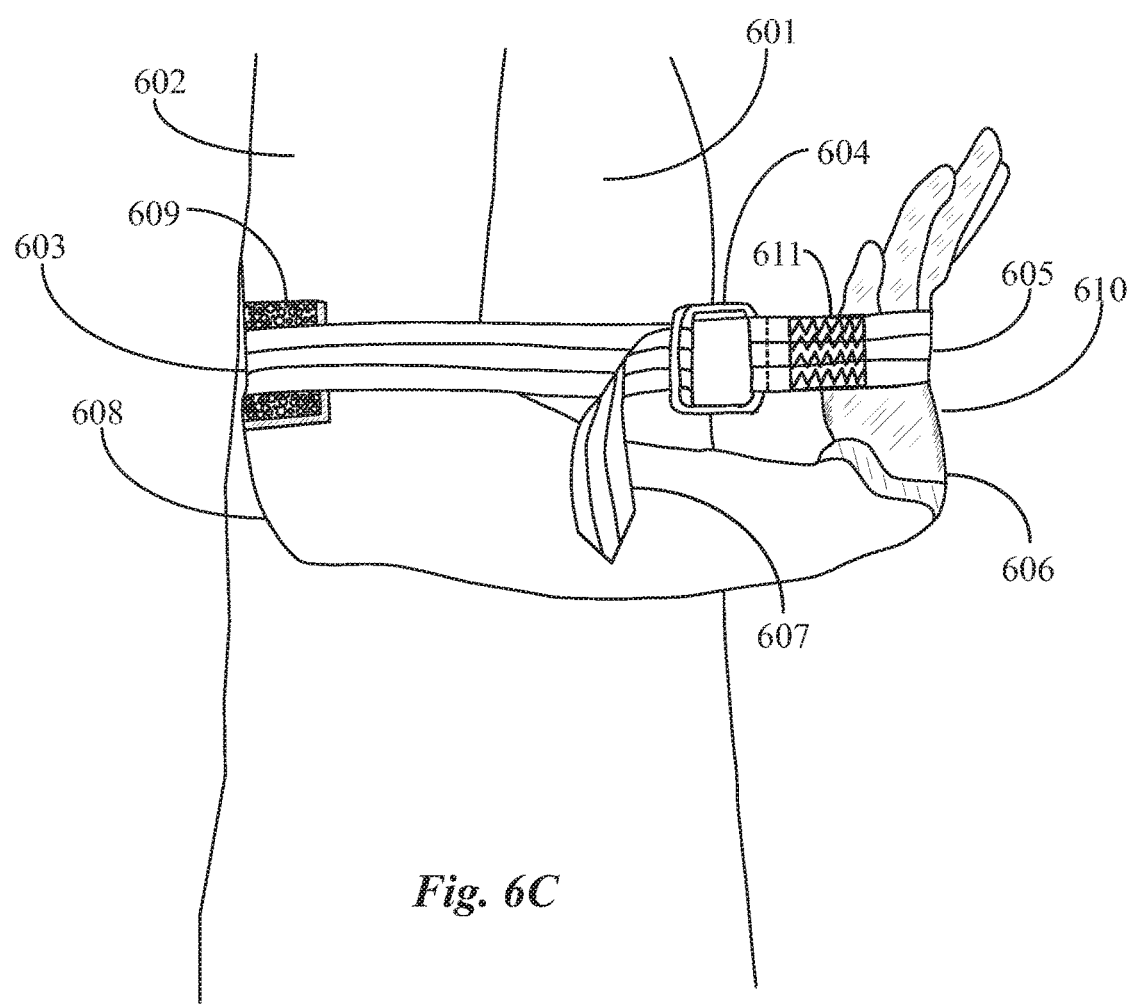
FIG. 6C is a perspective view of the apparatus with a relief patch and pad.

FIGS. 6A-6C shows a glove 610 specifically designed for use in the system. Glove 610 can be made from natural or synthetic material, for example silicon, rubber, cotton, polyester, leather, etc. Glove 610 that is made from a natural material may be lined with a no-slide material that adheres to human skin, for example flexible silicon or types of rubber. FIG. 6A shows a strip 611 of VELCRO™ or other material that will adhere to belt 607 at area 605. FIG. 6B shows an additional strip 611 of VELCRO™ or other material that will adhere to belt 607 in a stretch as shown in FIG. 2A. at area 205. Further glove 610 includes an elastic collar 606 that encompasses the users wrist as an aid to keep the glove in position during use. The embodiment of FIG. 6C depicts use of the belt in a stretch focusing on dorsal portions of the wrist where the belt 607 loops around the major knuckles at an area 603 over the pad 609, above the bent elbow 608 and below bicep 602. Belt 607 is closed with buckle 604 in this embodiment, but also could be the ratchet 507.

Figure 7:
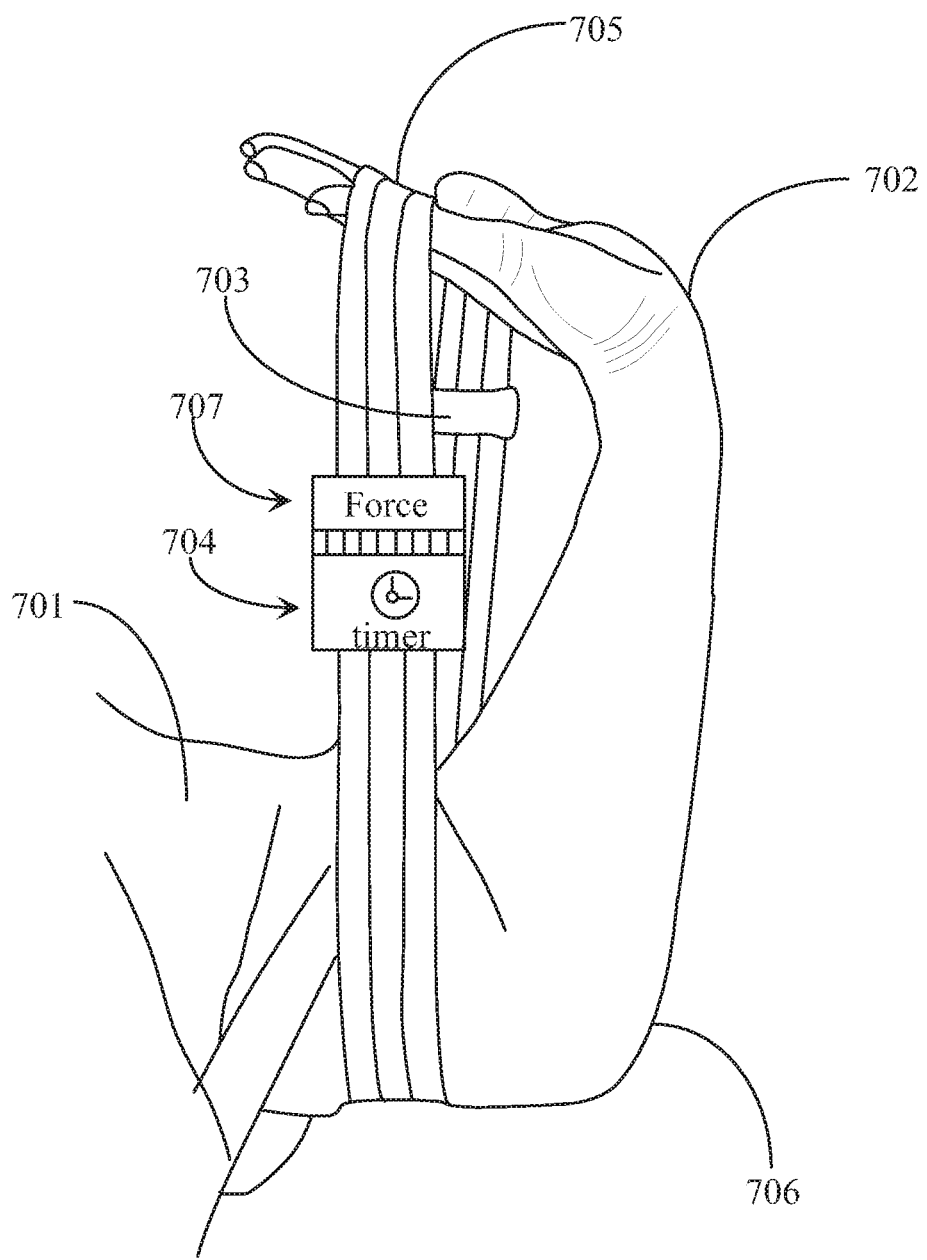
FIG. 7 is a perspective view of the apparatus implementing a torque meter and timer.

FIG. 7 shows an embodiment implementing a force or torque meter 707 including a timer 704. The torque meter 707 and timer 704 are shown as a single unit, but may be separate appliances. In another embodiment the timer could be a separate appliance not attached to the belt. It is to be understood to one with skill in the art that the belt is split creating two adjacent ends each attached to one of two adjacent bars or rods at the torque meter in order to track an amount of force being applied when tightening the belt 705 causing the two adjacent belt ends to pull the bars or rods apart. The torque meter and the timer may present reading in digital or analog format.

Figure 8:
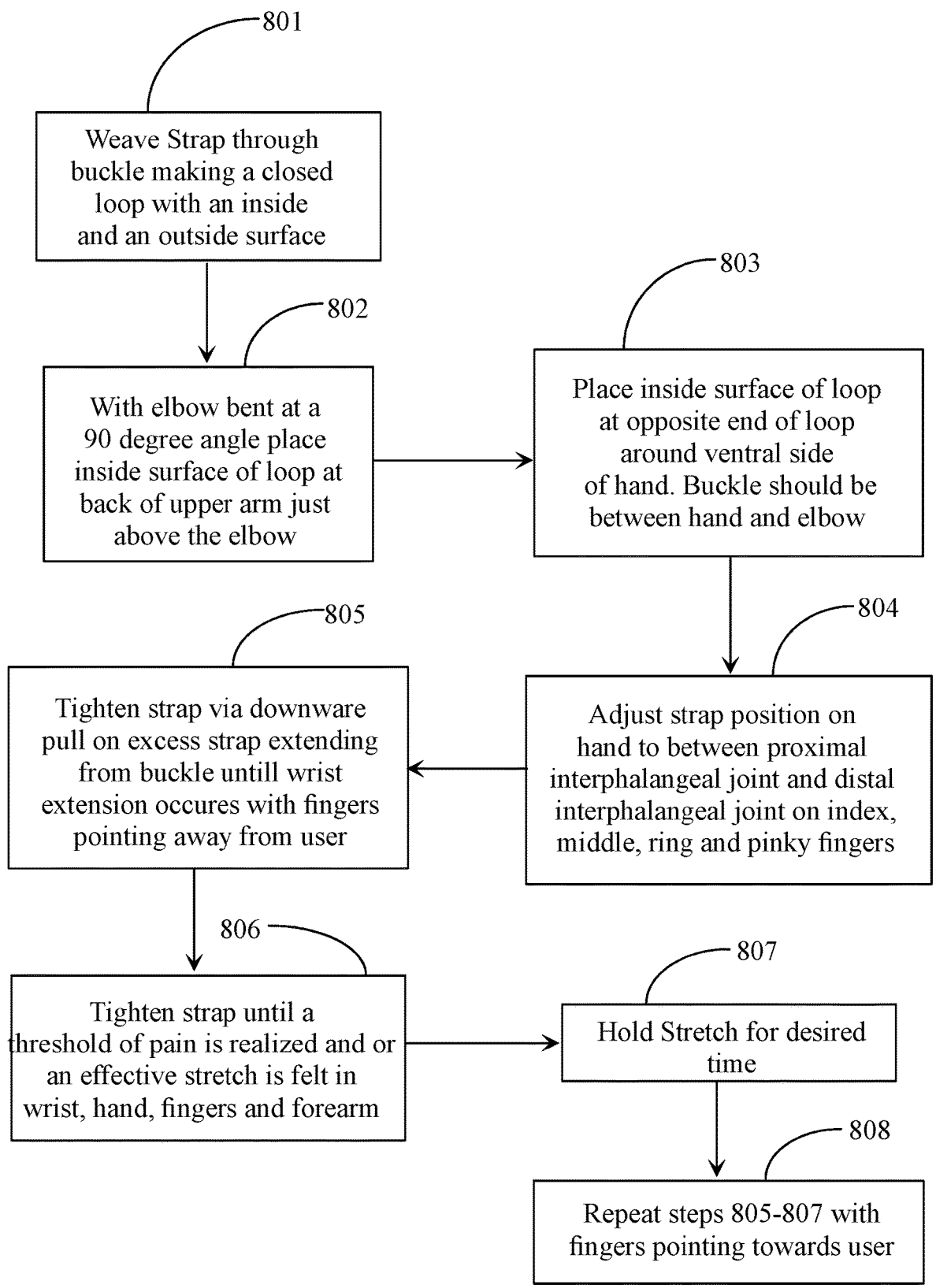
FIGS. 8-11 depict a method flow of embodiments implementing a method of using the apparatus.

FIG. 8 presents a flowchart of steps taken during use of the apparatus and method of one embodiment of the present invention. Step 801 the user weaves the strap or belt through a buckle, or through a ratchet used for tightening the belt, making a closed loop with an inside surface making contact with a user's arm and an outside surface. Next the elbow is bent at step 802 approximately 90 degrees, but may be within a range of 45-100 degrees as needed to fit the belt or strap properly, depending on flexibility of the user and type of stretch implemented. At step 803, with elbow bent at approximately a 90 degree angle, a user places the inside surface of loop at a back of upper arm at the tricep area, just above the elbow. The user then places the inside surface of the loop at an opposite end around the ventral side of a user's hand. The buckle or ratchet should be between hand and elbow. The strap position is adjusted at step 804 at the hand to between the proximal interphalangeal joint and distal interphalangeal joint on the index, middle, ring and pinky fingers.

The user tightens the strap at step 805 by tightening the strap or belt via pulling downward on excess strap of the strap extending from the buckle, or alternatively, the ratchet by manipulate handle 510 of the ratchet until wrist extension occurs with fingers pointing away from user. The strap or belt continues to be tightened at step 806 until a threshold of pain is realized and or an effective stretch is felt in wrist, hand, fingers and forearm. At step 807 the stretch is held for a desired time. At step 808 steps 805-807 could be repeated with the fingers pointed in an opposite direction towards the user.

Figure 9:
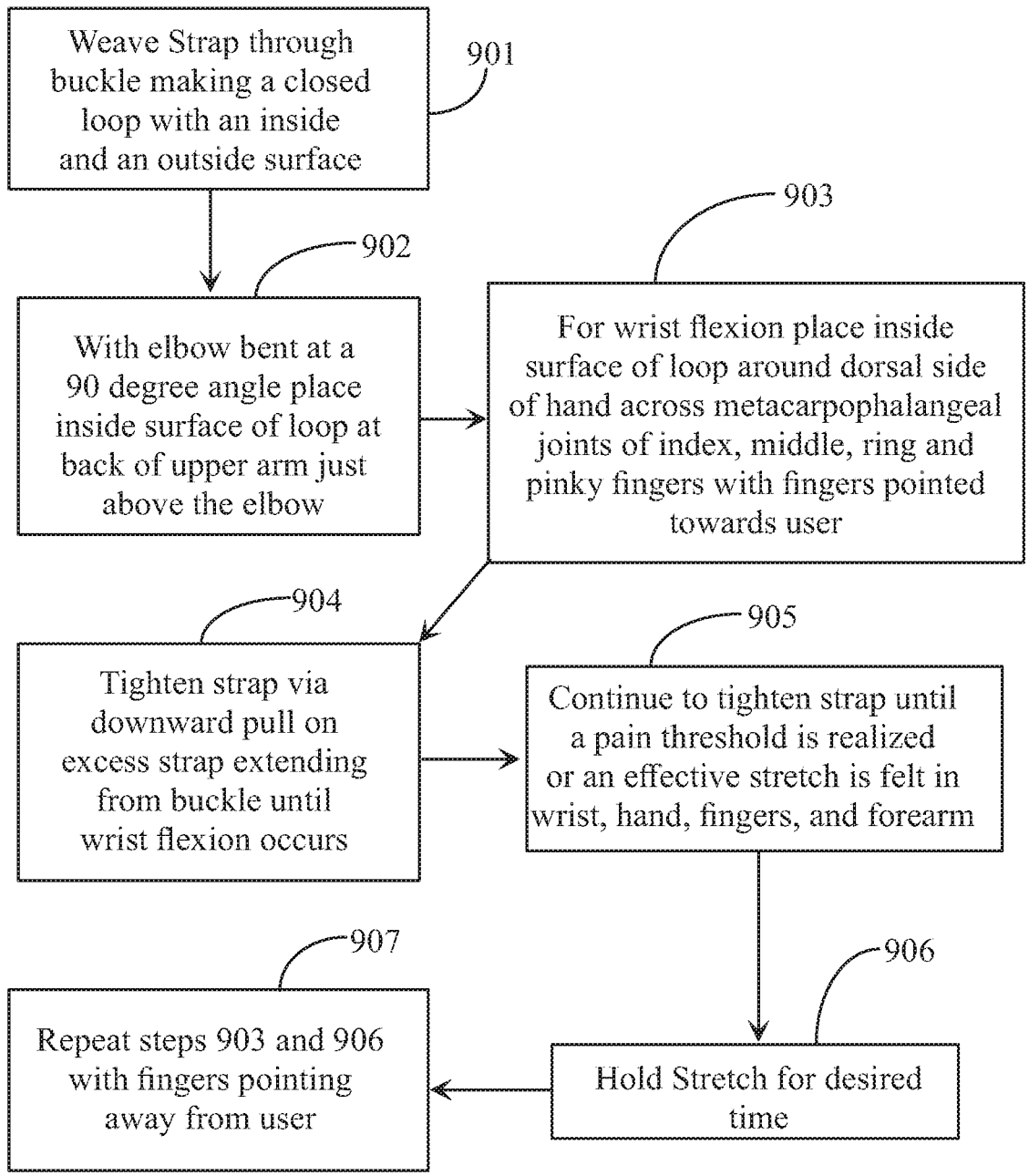

FIG. 9 represents a flow chart of a method using the apparatus in an alternate embodiment of the present invention. Step 901 begins by weaving the strap or belt through the buckle making a closed loop with an inside flat surface and an outside flat surface. With the user's elbow bent at approximately 90 degrees at step 902, the inside surface of the loop is placed at the back of the upper arm of the user at the tricep area just above the elbow. At step 903, in order to achieve a wrist flexion, the inside surface of the loop is placed around a dorsal side of the user's hand across the metacarpophalangeal joints of index, middle, ring and pinky fingers with fingers pointed towards user. The strap or belt is tightened at step 904 by a downward pull on an excess strap extending from the buckle until wrist flexion occurs. Alternatively the belt or strap is tightened via handle movement of the ratchet when the ratchet is used in place of the buckle. At step 905 the strap or buckle is continuously tightened until a pain threshold is realized or an effective stretch is felt in wrist, hand, fingers, and forearm. The user then holds the stretch for a predetermined or desired amount of time at step 906. Steps 903 and 906 are then repeated with the user's fingers pointed away from the user at step 907.

Figure 10:
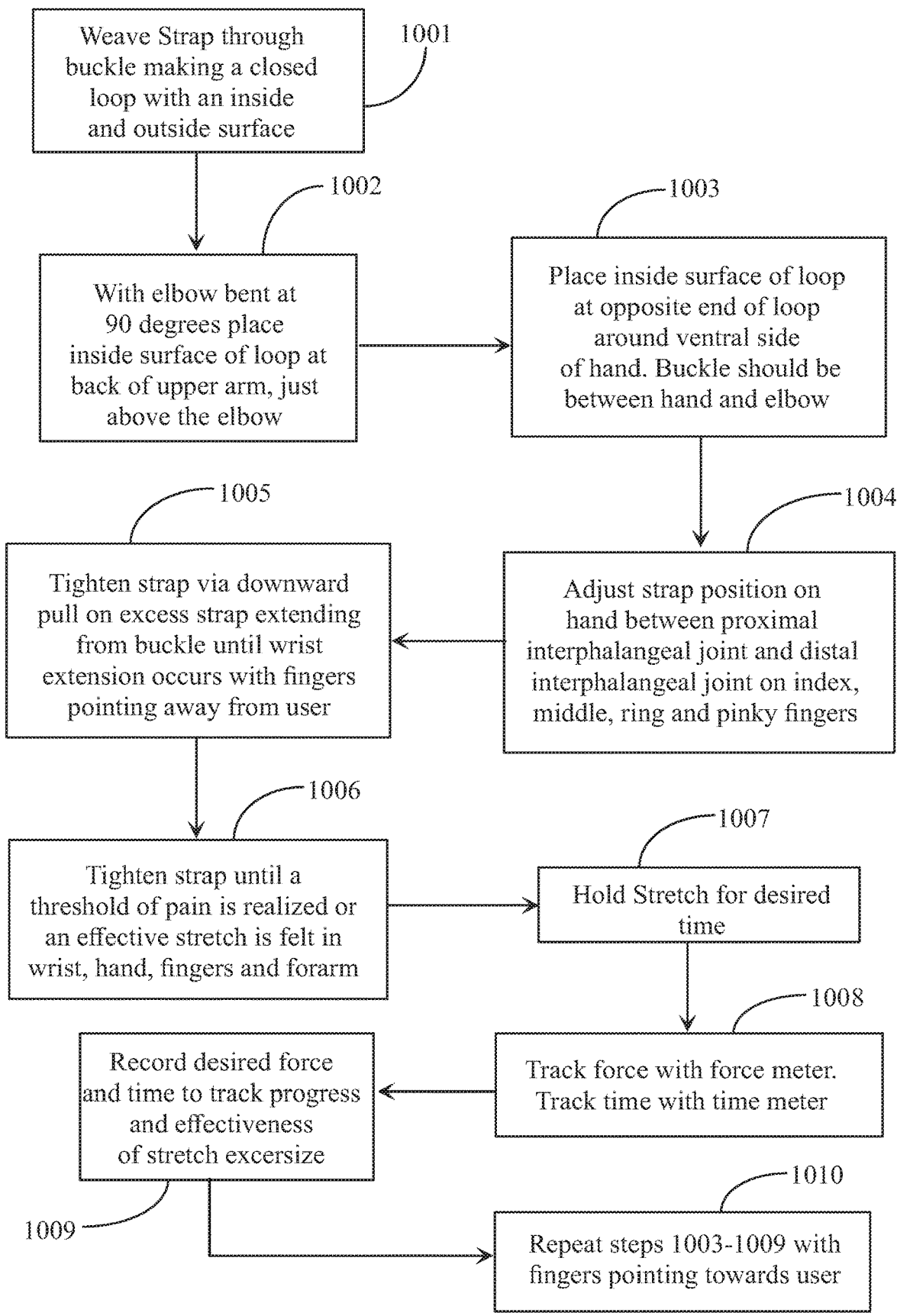

FIG. 10 begins with step 1001 where the strap or belt is weaved through the buckle or ratchet making a closed loop with an inside and outside surface. With the user's elbow bent at 90 degrees at step 1002, the inside surface of loop is positioned at the back of upper arm, at an area of the user's tricep, just above the elbow. The inside surface of the strap or belt, at an opposite end of the tricep position, is placed around the ventral side of the user's hand at step 1003. The buckle or ratchet should be between hand and elbow. At step 1004 the strap is positioned on the user's hand between the proximal interphalangeal joint and distal interphalangeal joint on the index, middle, ring and pinky fingers. The strap or belt is tightened at step 1005 via a downward pull on an excess strap extending from the buckle or ratchet until wrist extension occurs with the user's fingers pointing away from the user. The strap or belt is further tightened at step 1006 until a threshold of pain is realized or an effective stretch is felt in the user's wrist, hand, fingers and forearm. The stretch is then held at step 1007 until a desired time is achieved. At step 1008 the user may track force with the torque or force meter and the user may track amount of time with the timer or time meter. When the user tracks force and time at every use at step 1009, progress may be realized when pain decreases and a time frame the user can maintain the stretch increases. The user may also track what force and time periods are most effective for relief from pain or discomfort of specific conditions, mentioned above. At step 1010, steps 1003-1009 may be repeated as needed for increasing flexibility, strength and relieving pain.

Figure 11:
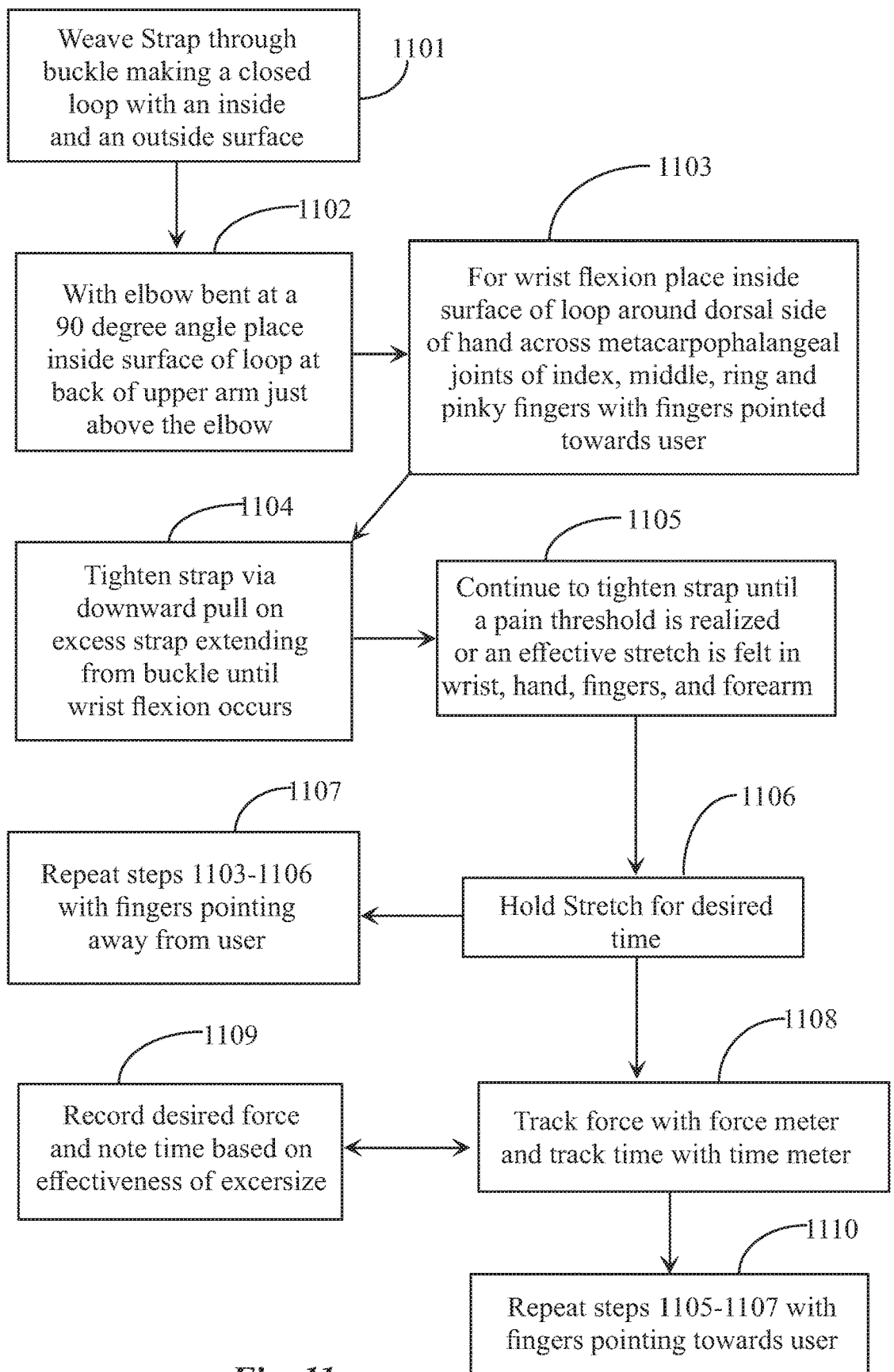

FIG. 11 begins by weaving the strap or belt through the buckle or ratchet of the apparatus at step 1101, making a closed loop with an inside and an outside surface. With the elbow bent at step 1102, at a 90 degree angle, the inside surface of the belt or strap is placed at the back of upper arm just above the elbow at an area incorporating the user's tricep. For wrist flexion, at step 1103, the inside surface of the loop is placed around the dorsal side of the user's hand across the metacarpophalangeal joints of index, middle, ring and pinky fingers with the user's fingers pointed towards user. The strap or belt is tightened at step 1104, via a downward pull at an excess strap extending from the buckle or ratchet until wrist flexion occurs. At step 1105, the user continues to tighten strap until a pain threshold is realized or an effective stretch is felt in the wrist, hand, fingers, and forearm. The stretch is held for a specific amount of time at step 1106. Force and time can be tracked at step 1108. Alternatively, the user may repeat steps 1103-1106 with the user's fingers pointing away from the user. At step 2220, steps 1105-1107 may be repeated with the user's fingers pointed towards the user, as needed.

The inventor of the present invention is a professional basketball player diagnosed with arthritis in the hands and wrists, and has found, through experience, that holding stretches for 5-30 minutes is most effective for treating at least arthritis. The force used is measured in pounds and varies per individual. The inventor began methodic stretching soon realizing the difficulty in holding various stretches for time periods required for increasing flexibility, strength and relieving pain. For other ailments, such as carpal tunnel syndrome and others, in order to keep the hands, wrists, fingers and forearms in good condition, shorter time windows and increased repetitions may be more beneficial.

Because the tendons and muscles in the hands and wrists are trying to return to their original state, soreness in the affected areas are normal, during and after use. After a few sessions of practicing the present methods with the apparatus, soreness should diminish. The present apparatus and method will work to strengthen the muscles in the wrists and hands; it has proven to relieve numbness in the fingers and increase flexibility with proper use. In one example of repetitive use of the apparatus and method, wrist flexion is achieved implementing three sets of ten to fifteen repetitions, with at least one minute of rest in between sets. For wrist extension, three sets of ten to fifteen repetitions, with at least one minute of rest in between sets.

It will be apparent to one with skill in the art, that the embodiments described above are specific examples of a single broader invention which may have greater scope than any of the singular descriptions taught. There may be many alterations made in the descriptions without departing from the spirit and scope of the present invention.

The invention claimed is:

1. A method for relieving at least carpal tunnel syndrome, arthritis and other ailments of a user's hands, wrist and forearm, comprising the steps of:
   (a) providing a single strap having a length enabled to encircle one side of a user's hand and tricep area of the user's arm when the user's elbow is bent at approximately 90°;

(b) creating a loop with the single strap, the loop having an inside flat surface and an outside flat surface;

(c) closing the loop with a buckle, weaving one end of the single strap through the buckle and securing a second end of the single strap at the buckle;

(d) positioning the inside flat surface of one end of the loop around a portion of a user's hand at an area crossing the user's proximal interphalangeal joint and distal interphalangeal joint on index, middle, ring and pinky fingers and positioning the inside flat surface of a second end of the loop around at an area at a back side of the user's upper arm, above the elbow;

(e) tightening the single strap to achieve an effective stretch as determined by the user; and (f) holding the stretch for a predetermined or desired amount of time and repeating steps (a)-(f) as required to increase strength and flexibility and lessen pain in the user's hand, wrist and forearm.

2. The method of claim 1, wherein positioning in step (d) occurs with the user's fingers pointed towards the user for the predetermined or desired amount of time and then the fingers are pointed away from the user for the predetermined or desired amount of time.

3. The method of claim 2, wherein, in step (d), the loop is placed around a ventral side of the portion of the user's hand for the predetermined or desired amount of time, and then placed on a dorsal side of a user's hand across an area including the user's metacarpophalangeal joints of index, middle, ring and pinky fingers for the predetermined or desired amount of time.

4. The method of claim 1, wherein a pad is implemented between the inside flat surface of the single strap and the area at a back side of the user's upper arm, above the elbow.

5. The method of claim 1, wherein the strap is connected at one end to a ratchet thereby replacing the buckle, and a second end is weaved through the ratchet enabling a handle of the ratchet to manipulate movement of the second end causing the single strap to tighten, holding the second end of the single strap in place, thereby decreasing a circumference of the loop.

6. The method of claim 1, wherein a torque or force meter is attached on the single strap enabling force in pounds to be determined as a result of tightening.

7. The method of claim 1, wherein a timer is implemented in order to record a time frame while the user holds the stretch.

8. The method of claim 1 wherein a glove is implemented on the user's hand prior to positioning in step (d).

9. The method of claim 8, wherein the glove is made from material that adheres to the user's skin and includes a hook and loop fastening strip between the single strap and an area on the glove.

* * * * *